(12) United States Patent
Burmistrov et al.

(10) Patent No.: US 11,383,640 B2
(45) Date of Patent: Jul. 12, 2022

(54) TECHNIQUES FOR AUTOMATICALLY REDUCING ANNOYANCE LEVELS OF DRIVERS WHEN USING DRIVER MONITORING SYSTEMS

(71) Applicant: HARMAN INTERNATIONAL INDUSTRIES, INCORPORATED, Stamford, CT (US)

(72) Inventors: Evgeny Burmistrov, Saratoga, CA (US); Stefan Marti, Oakland, CA (US); Joseph Verbeke, San Francisco, CA (US); Priya Seshadri, San Francisco, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 8 days.

(21) Appl. No.: 17/031,635

(22) Filed: Sep. 24, 2020

(65) Prior Publication Data

US 2022/0089086 A1    Mar. 24, 2022

(51) Int. Cl.
*B60Q 1/00* (2006.01)
*B60Q 9/00* (2006.01)
(Continued)

(52) U.S. Cl.
CPC .............. *B60Q 9/00* (2013.01); *A61B 5/0205* (2013.01); *A61B 5/1107* (2013.01); *A61B 5/165* (2013.01); *A61B 5/18* (2013.01); *A61B 5/4803* (2013.01); *A61B 5/7264* (2013.01); *A61B 5/7405* (2013.01); *A61B 5/746* (2013.01); *A61B 5/7455* (2013.01); *G06V 20/59* (2022.01); *G06V 40/176* (2022.01); *A61B 5/024* (2013.01); *A61B 5/0533* (2013.01)

(58) Field of Classification Search
CPC ....... B60Q 9/00; A61B 5/0205; A61B 5/1107; A61B 5/165; A61B 5/18; A61B 5/4803; A61B 5/7264; A61B 5/7405; A61B 5/7455; A61B 5/746; A61B 5/024; A61B 5/0533; G06K 9/00315; G06K 9/00832
USPC ........................................................ 340/439
See application file for complete search history.

(56) References Cited

U.S. PATENT DOCUMENTS

11,191,468 B2 * 12/2021 Nashida .................... A61B 5/18
2002/0041692 A1 * 4/2002 Seto ........................ G06F 16/636
(Continued)

*Primary Examiner* — Zhen Y Wu
(74) *Attorney, Agent, or Firm* — Artegis Law Group, LLP (57) ABSTRACT

In various embodiments, an alert personalization application personalizes in-vehicle alerts. The alert personalization application estimates an increase in a negative emotion associated with an occupant of a vehicle based on at least one characteristic of the occupant. Subsequently, the alert personalization application determines that the increase is associated with a negative reaction to an in-vehicle alert that has a first alert characteristic. In response, the alert personalization application determines that the first alert characteristic should be replaced with a second alert characteristic. The alert personalization causes another in-vehicle alert to be generated that has the second alert characteristic instead of the first alert characteristic. Advantageously, personalizing alert characteristics that influence how and/or when in-vehicle alerts are generated can increase the effectiveness of in-vehicle alerts and can improve driving safety.

20 Claims, 3 Drawing Sheets

(51) Int. Cl.
*A61B 5/16* (2006.01)
*A61B 5/18* (2006.01)
*A61B 5/00* (2006.01)
*A61B 5/11* (2006.01)
*A61B 5/0205* (2006.01)
*G06V 20/59* (2022.01)
*G06V 40/16* (2022.01)
*A61B 5/024* (2006.01)
*A61B 5/0533* (2021.01)

(56) References Cited

U.S. PATENT DOCUMENTS

| | | | |
|---|---|---|---|
| 2015/0053066 A1* | 2/2015 | Hampiholi | G10H 1/0008 84/602 |
| 2018/0029612 A1* | 2/2018 | Tsuyunashi | B60W 40/04 |
| 2020/0000392 A1* | 1/2020 | Nashida | G01C 21/3641 |
| 2020/0082287 A1* | 3/2020 | Beaurepaire | G06N 5/047 |
| 2020/0152197 A1* | 5/2020 | Penilla | G10L 25/63 |
| 2020/0239003 A1* | 7/2020 | Sobhany | B60K 35/00 |
| 2020/0239005 A1* | 7/2020 | Zijderveld | B60W 50/14 |
| 2020/0269865 A1* | 8/2020 | Yoon | A61B 5/18 |
| 2020/0311475 A1* | 10/2020 | el Kaliouby | G06K 9/6256 |

* cited by examiner

TECHNIQUES FOR AUTOMATICALLY REDUCING ANNOYANCE LEVELS OF DRIVERS WHEN USING DRIVER MONITORING SYSTEMS

BACKGROUND

Field of the Various Embodiments

The various embodiments relate generally to computer science, software engineering, and automotive systems and, more specifically, to techniques for automatically reducing annoyance levels of drivers when using driver monitoring systems.

Description of the Related Art

Driver monitoring systems are intended to increase driving safety and improve the overall driving experiences of drivers. In operation, a typical driver monitoring system ("DMS") detects and generates alerts when a driver is drowsy, distracted, etc. A typical DMS includes a DMS application and a variety of sensors that monitor physiological characteristics of the driver. Based on the sensor data, the DMS application determines whether to alert the driver to potentially unsafe behavior. For example, a DMS application could analyze the eye gaze direction of a driver based on sensor data received from an in-vehicle camera to determine that the driver is not looking at the road. The DMS application could then generate an in-vehicle alert warning the driver that he or she is not properly focused on the road.

One drawback of DMS applications is that, because DMS applications do not usually take into account different driving scenarios and driving styles, DMS applications can repeatedly generate in-vehicle alerts that become annoying to drivers and cause drivers to not pay attention to the in-vehicle alerts or stop using the DMSs altogether. For example, while a driver is backing up a vehicle and looking at a rear view mirror for guidance, a DMS application could repeatedly generate in-vehicle alerts warning the driver that he or she is not looking at the road. The driver could become frustrated and/or annoyed at the in-vehicle alerts and either turn off the DMS or disregard all in-vehicle alerts on a going-forward basis. Turning off the DMS or disregarding in-vehicle alerts defeats the purpose of having and using the DMS to increase driving safety.

Another drawback of DMS applications is that a typical DMS application generates in-vehicle alerts that are characterized by a predetermined delivery modality, a predetermined intensity, and/or a predetermined minimum repetition interval that are effective for only some drivers. Other drivers might find in-vehicle alerts characterized by these predetermined "alert characteristics" irritating and/or distracting and, as a result, ignore in-vehicle alerts or disable the DMS.

As the foregoing illustrates, what is needed in the art are more effective techniques for generating in-vehicle alerts.

SUMMARY

One embodiment sets forth a computer-implemented method for generating personalized in-vehicle alerts. The method includes estimating an increase in a negative emotion associated with an occupant of a vehicle based on at least one characteristic of the occupant; determining that the increase is associated with a negative reaction to a first in-vehicle alert that has a first alert characteristic; in response, determining that the first alert characteristic should be replaced with a second alert characteristic; and causing at least a second in-vehicle alert to be generated that has the second alert characteristic instead of the first alert characteristic.

At least one technical advantage of the disclosed techniques relative to the prior art is that the disclosed techniques personalize current and subsequent in-vehicle alerts based on the physiological responses of individual drivers to prior in-vehicle alerts. In particular, automatically detecting when an in-vehicle alert causes the annoyance level of a driver to increase and, in response, modifying an alert characteristic that influences how and/or when in-vehicle alerts are generated can increase the effectiveness of current and subsequent in-vehicle alerts. Among other things, modifying the alert characteristic can reduce the likelihood that the driver becomes annoyed at the in-vehicle alerts and either turns off the DMS or disregard all in-vehicle alerts on a going-forward basis. Thus, by implementing the disclosed techniques in conjunction with a driving monitoring system, driving safety can be improved across a wider variety of drivers relative to prior art approaches. These technical advantages provide one or more technological advancements over prior art approaches.

BRIEF DESCRIPTION OF THE DRAWINGS

So that the manner in which the above recited features of the various embodiments can be understood in detail, a more particular description of the inventive concepts, briefly summarized above, may be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

DETAILED DESCRIPTION

In the following description, numerous specific details are set forth to provide a more thorough understanding of the various embodiments. However, it will be apparent to one skilled in the art that the inventive concepts may be practiced without one or more of these specific details.

System Overview

Figure 1:
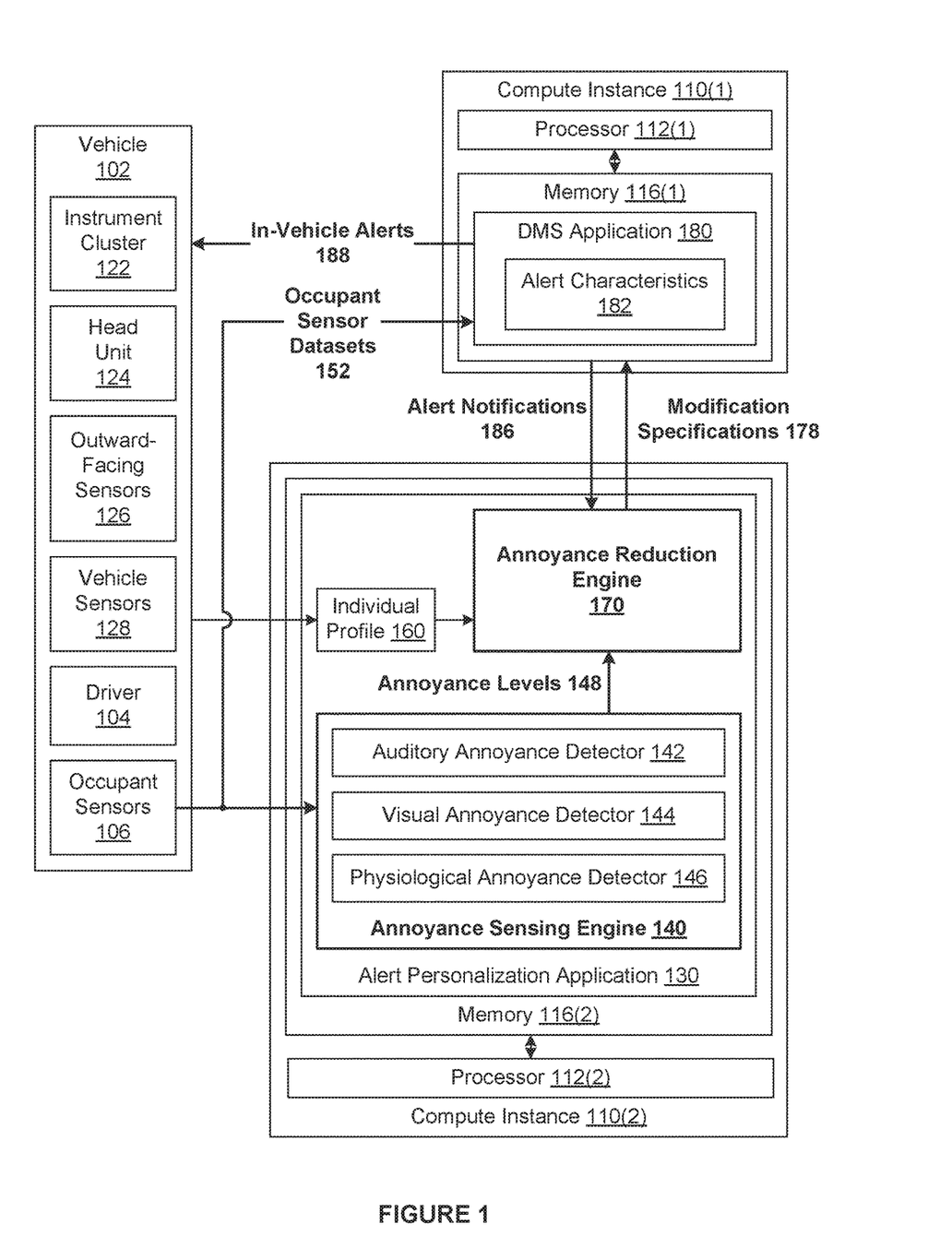
FIG. 1 is a conceptual illustration of a system configured to implement one or more aspects of the various embodiments.

FIG. 1 is a conceptual illustration of a system 100 configured to implement one or more aspects of the various embodiments. As shown, in some embodiments, the system 100 includes, without limitation, a compute instance 110(1), a compute instance 110(2), and a vehicle 102. For explanatory purposes, multiple instances of like objects are denoted with reference alphanumeric characters identifying the object and parenthetical alphanumeric characters identifying the instance where needed.

In some embodiments, the system 100 can include any number of compute instances 110, any number of vehicles 102, and any number of additional components (e.g., applications, subsystems, modules, etc.) in any combination. Any number of the components of the system 100 can be distributed across multiple geographic locations or implemented in one or more cloud computing environments (i.e., encapsulated shared resources, software, data, etc.) in any combination.

As shown, the compute instance 110(1) includes, without limitation, a processor 112(1) and a memory 116(1), and the compute instance 110(2) includes, without limitation, a processor 112(2) and a memory 116(2). The compute instances 110(1) and 110(2) are also referred to herein individually as "the compute instance 110" and collectively as "the compute instances 110." The processors 112(1) and 112(2) are also referred to herein individually as "the processor 112" and collectively as "the processors 112." The memories 116(1) and 116(2) are also referred to herein individually as "the memory 116" and collectively as "the memories 116." Each of the compute instances 110 can be implemented in a cloud computing environment, implemented as part of any other distributed computing environment, or implemented in a stand-alone fashion.

The processor 112 can be any instruction execution system, apparatus, or device capable of executing instructions. For example, the processor 112 could be a central processing unit, a graphics processing unit, a controller, a microcontroller, a state machine, or any combination thereof. The memory 116 of the compute instance 110 stores content, such as software applications and data, for use by the processor 112 of the compute instance 110. The memory 116 can be one or more of a readily available memory, such as random-access memory, read only memory, floppy disk, hard disk, or any other form of digital storage, local or remote. In some embodiments, each of any number of compute instances 110 can include, without limitation, any number of processors 112 and any number of memories 116 in any combination. In particular, any number of the compute instances 110 (including one) can provide a multiprocessing environment in any technically feasible fashion.

In some embodiments, a storage (not shown) can supplement or replace the memory 116. The storage can include, without limitation, any number and/or types of external memories that are accessible to the processor 112. For example, and without limitation, the storage can include a Secure Digital Card, an external Flash memory, a portable compact disc read-only memory (CD-ROM), an optical storage device, a magnetic storage device, or any suitable combination of the foregoing.

Each of the compute instances 110 is configured to implement one or more software applications. For explanatory purposes only, each software application is depicted as residing in the memory 116 of one of the compute instances 110 and executing on the processor 112 of the compute instance 110. However, in some embodiments, the functionality of each software application may be distributed across any number of other software applications that reside in the memories 116 of any number of compute instances 110 and execute on the processors 112 of any number of compute instances 110 in any combination. Further, the functionality of any number of software applications can be consolidated into a single software application.

The vehicle 102 can be any type of ground-based or non-ground-based machine that is guided, at least in part, by a driver 104 that can be any human. In some embodiments, the vehicle 102 can be, among other things, a car, a motorcycle, a sport utility vehicle, a truck, a bus, an all-terrain vehicle, a snowmobile, a commercial construction machine (e.g., a crane, an excavator, etc.), an airplane, a helicopter, or a boat. In the same or other embodiments, the vehicle 102 can be a taxi, a ride share vehicle (such as an Uber vehicle, a Lyft vehicle), a submarine, an electric vertical takeoff and landing vehicle, a spaceship, etc.

As shown, the vehicle 102 includes, without limitation, an instrument cluster 122, a head unit 124, any number of outward-facing sensors 126, any number of vehicle sensors 128, and any number of occupant sensors 106. The vehicle 102 can additionally include any number and/or types of vehicle components that enable the driver 104 to perform a primary driving task as well as any number and/or types of vehicle components that enable the driver 104 and/or other occupants of the vehicle 102 to perform secondary tasks. Examples of vehicle components that implement the primary driving task include, without limitation, brakes, a powertrain, a transmission, and a steering system. Examples of vehicle components that enable the driver 104 and passengers to perform secondary tasks include, without limitation, a radio, a temperature control system, a navigation system, an in-car internet system, etc.

The instrument cluster 122 and the head unit 124 enable the driver 104 to monitor and/or modify one or more functionalities of the vehicle 102. As referred to herein, the functionalities of the vehicle 102 include, without limitation, operations of the vehicle 102 that are associated with driving the vehicle 102 and any type of actions that are associated with any number of secondary tasks. Examples of functionalities of the vehicle 102 includes, without limitation, the speed of the vehicle 102, the direction of the vehicle 102, information being output on any number of a visual display, an auditory display, and/or a haptic display within the vehicle 102, etc. In some embodiments, the vehicle 102 can include any number of components instead of or in addition to the instrument cluster 122 and the head unit 124 that enable the driver 104 to monitor and/or modify the functionalities of the vehicle 102. For instance, in some embodiments, the vehicle 102 includes a rear-view camera.

The instrument cluster 122 includes, without limitation, any number and type of analog components and any number and type of digital components that aggregate and display data from various components of the vehicle 102. For instance, in some embodiments, the instrument cluster 122 includes, without limitation, an analog speedometer, a digital dashboard, and the compute instance 110(3) (not shown) that executes a trip computer application. The digital dashboard can display any amount and type of data related to the vehicle 102, such as a fuel level, an interior temperature, an exterior temperature, and a distance traveled. The trip computer application can record and display any number of statistics related to the vehicle 102. In some embodiments, the trip computer application records and displays an average speed, an average distance traveled, an average fuel consumption, an estimated range, and so forth.

The head unit 124 enables the driver 104 to efficiently perform both the primary driving task and certain secondary tasks. In some embodiments, the head unit 124 includes, without limitation, a hardware interface to an infotainment system and a navigation system. In the same or other embodiments, the hardware interface includes, without limitation, a touch-screen and any number and combination of input mechanisms, output mechanisms, and control mechanisms (e.g., buttons, sliders, etc.). In some embodiments, the hardware interface includes, without limitation, built-in Bluetooth for hands-free calling and audio streaming, universal serial bus ("USB") connections, speech recognition, rearview camera inputs, video outputs for any number and type of displays, and any number of audio outputs. In general, any number of sensors, displays, receivers, transmitters, etc., can be integrated into the head unit 124 or can be implemented externally to the head unit 124. External devices can communicate with the head unit 124 in any technically feasible fashion.

The outward-facing sensors 126 and the vehicle sensors 128 monitor, respectively, the area surrounding the vehicle 102 and the vehicle 102 itself while the vehicle 102 operates. Some examples of the outward-facing sensors 126 include, without limitation, a forward-facing camera that is mounted on the vehicle 102, a light detection and ranging sensor, etc. The outward-facing sensors 126 are also referred to herein individually as "the outward-facing sensor 126." In some embodiments, the vehicle sensors 128 include, without limitation, any number and/or types of sensors that monitor different characteristics of the vehicle 102 and/or any number and/or types of sensors that monitor inputs to the vehicle 102. Some examples of characteristics of the vehicle 102 includes, without limitation, the speed, the lateral acceleration, the engine revolutions per minute, the battery charge state, and so forth. Some examples of inputs to the vehicle 102 includes, without limitation, the current steering wheel angle, the accelerator pedal position, the brake pedal position, etc. The vehicle sensors 128 are also referred to herein individually as "the vehicle sensor 128."

The occupant sensors 106 monitor the driver 104 and optionally any number of other occupants of the vehicle 102. The occupant sensors 106 include, without limitation, any number and/or types of devices that detect and relay any quantifiable aspect of a human being in any technically feasible. The occupant sensors 106 can be distributed across various locations. In some embodiments, each of the occupant sensors 106 is attached to the vehicle 102 (e.g., built into a steering wheel, headrest, etc.) or worn by an occupant of the vehicle 102. The occupant sensors 106 are also referred to herein individually as "the occupant sensor 106."

Although not shown, in some embodiments, the occupant sensors 106 include, without limitation, any number of head sensors, any number of eye sensors, any number of audio sensors, any number of body sensors, any number of skin sensors, and any number of neural sensors that, in real-time, detect and relay physiological data (e.g., measurements) associated with the driver 104 and any number of other occupants of the vehicle 102.

The head sensors include, without limitation, any number and combination of optical sensors (e.g., visible light cameras, infrared light cameras, depth sensors, etc.), magnetic sensors, blood flow sensors, muscle contraction sensors, thermal sensors, radar sensors, and any other technically feasible type of physiological sensor via which the position and/or orientation of the head of a human being (i.e., a head position and/or a head orientation, respectively) can be determined.

The eye sensors include, without limitation, any number and combination of an eye gaze direction module, a vergence sensor, a pupillometry sensor, an optical depth sensor, or any other technically feasible type of physiological sensor via which the gaze direction and/or eye convergence distance of a human being can be determined. The audio sensors include, without limitation, any number and types of a microphone, microphone array, or any other technically feasible type of sensor via which words and/or sounds associated with a human being can be determined.

The body sensors include, without limitation, any number and combination of optical sensors via which the gesticulation and/or posture of a human being can be determined, musculature sensors via which the muscle contractions of a human being can be determined, breathing rate sensors via which the breathing rate of a human being can be determined, heart rate sensors via which of electrocardiogram readings of a human being can be determined, pulse oximeters via which the pulse rate of a human being can be determined, weight sensors during which the weight distribution of any number of human beings can be determined, and any other technically feasible types of physiological sensors via which any quantifiable aspects of the body of a human being (e.g., a body position, a body orientation, etc.) can be determined.

The skin sensors include, without limitation, any number and combination of a galvanic skin response sensor, a skin conduction sensor, a skin texture sensor, or any other technically feasible type of physiological sensor via which at least one characteristic of the skin of a human being (e.g., a skin conductivity) can be quantified. The neural sensors include, without limitation, any number and combination of a neural activity measurement device (e.g., an electroencephalogram sensor), a functional magnetic resonance imaging unit, an optogenetics module, or any other technically feasible type of physiological sensor via which any form of human neural activity can be quantified.

To increase driving safety and improve the overall driving experiences of the driver 104, the system 100 implements a DMS (not explicitly shown) that includes, without limitation, the occupant sensors 106 and a DMS application 180. In some embodiment, the DMS application 180 resides in the memory 116(1) of the compute instance 110(1) and executes on the processor 112(1) of the compute instance 110(1). As shown, in some embodiments, the compute instance 110(1) is external to the vehicle 102. In some other embodiments, the computer instance 110(1) is internal to the vehicle 102. In the same or other embodiments, the compute instance 110(1) can be integrated into the vehicle 102 in any technically feasible fashion. For instance, in some embodiments, the compute instance 110(1) is included in the instrument cluster 122. In some embodiments, the DMS can include, without limitation, any number and/or types of DMS applications 180 that reside in the memories 116 of any number of compute instances 110 and execute on the processors 112 of any number of compute instances 110 in any combination.

In some embodiments, as the vehicle 102 operates, the DMS application 180 continually or repeatedly receives any number and/or types of occupant sensor datasets 152 from the occupant sensors 106. The occupant sensor datasets 152 are also referred to herein individually as "the occupant sensor dataset 152." In some embodiments, each of the occupant sensor datasets 152 is associated with the occupant sensor 106 that generated the occupant sensor dataset 152 and a timestamp that indicates the point it time at which the occupant sensor 106 generated the occupant sensor dataset 152. In the same or other embodiments, each of the occupant sensor datasets 152 is associated with any number of the occupants of the vehicle 102 in any technically feasible fashion.

In some embodiments, the vehicle 102, any number of the occupant sensors 106, any number of other components included in the vehicle 102, or any combination thereof can transmit any number and/or types of the occupant sensor datasets 152 to any number of software applications (including the DMS application 180) in any technically feasible fashion. In the same or other embodiments, the DMS application 180 can acquire any number and/or types of the occupant sensor datasets 152 from any number of software applications, the vehicle 102, any number of the occupant sensors 106, any number of other components included in the vehicle 102, or any combination thereof in any technically feasible fashion.

The DMS application 180 estimates and/or monitors any number and/or types of behavior and/or characteristics associated with any number of the occupants of the vehicle 102 based on the occupant sensor datasets 152 in any technically feasible fashion. In some embodiments, the DMS application 180 performs any number and/or types of eye lid analysis operations based on any number of the occupant sensor datasets 152 to estimate and monitor the fatigue level of the driver 104. In the same or other embodiments, the DMS application 180 performs any number and/or types of eye gaze direction analysis operations based on any number of the occupant sensor datasets 152 to estimate and monitor the distraction level of the driver 104.

As the vehicle 102 operates, the DMS application 180 continually and/or repeatedly determines whether and/or how to generate any number and/or types of in-vehicle alerts 188 based, at least in part, on the behavior and/or characteristics associated with the occupants of the vehicle 102. The in-vehicle alerts 188 are also referred to herein individually as "the in-vehicle alert 188." Each of the in-vehicle alerts 188 notifies at least one occupant of the vehicle 102 of undesirable and/or potentially unsafe behavior and/or characteristics associated with any number of the occupants of the vehicle 102. In some embodiments, each of the in-vehicle alerts 188 is intended to notify the driver 104 of undesirably and/or potentially unsafe behavior and/or characteristics associated with the driver 104.

As shown, in some embodiments, the DMS application 180 includes, without limitation, any number and/or types of alert characteristics 182. The alert characteristics 182 are also referred to herein individually as "alert characteristic 182." Each of the alert characteristics 182 influences at least one aspect of how and/or when the DMS application 180 generates the in-vehicle alerts 188. Although not shown, in some embodiments, the alert characteristics 182 include, without limitation, a characteristic that is a delivery modality, a characteristic that is an intensity, and a characteristic that is a minimum repetition interval. A characteristic that is a delivery modality is also referred to herein as a "delivery modality characteristic," a characteristic that is an intensity is also referred to herein as an "intensity characteristic," and a characteristic that is a minimum repetition interval is also referred to herein as a "minimum repetition interval characteristic." For example, the alert characteristics 182 could include, without limitation, a delivery modality characteristic of female voice transmission, an intensity characteristic of high, and a minimum repetition interval characteristic of five seconds. Accordingly, the DMS application 180 generates verbal in-vehicle alerts using a female voice speaking at a loud volume at a minimum repetition interval of five seconds.

The DMS application 180 can cause the vehicle 102 to issue each of the in-vehicle alerts 188 in any technically feasible fashion. As shown, in some embodiments, the DMS application 180 transmits the in-vehicle alerts 188 to the vehicle 102. Each of the in-vehicle alerts 188 can be associated with any component included in the vehicle 102 and can cause the associated component to issue the in-vehicle alert 188 in any technically feasible fashion. For example, the in-vehicle alert 188 could be an audio signal that is transmitted to a speaker or speaker system included in the vehicle 102 that, upon receiving the audio signal, issues the in-vehicle alert 188 verbally.

As described previously herein, one drawback of conventional DMS applications is that conventional DMS applications can repeatedly generate in-vehicle alerts that become annoying to drivers and cause drivers to not pay attention to the in-vehicle alerts or stop using the DMSs altogether. Another drawback of conventional DMS applications is that a typical conventional DMS application generates in-vehicle alerts based on predetermined alert characteristics that are effective for only some drivers. Other drivers might find in-vehicle alerts characterized by these predetermined alert characteristics irritating and/or distracting and, as a result, ignore in-vehicle alerts or disable the DMS.

Tailoring In-Vehicle Alerts to Individual Drivers

To address the above problems, the system 100 includes, without limitation, an alert personalization application 130 that automatically causes the DMS application 180 to modify any number of the alert characteristics 182 to reduce negative reactions of one or more of the occupants to the in-vehicle alerts 188. As shown, in some embodiments, the alert personalization application 130 resides in the memory 116(2) of the compute instance 110(2) and executes on the processor 112(2) of the compute instance 110(2). In some embodiments, the compute instance 110(2) is external to the vehicle 102. In some other embodiments, the computer instance 110(2) is internal to the vehicle 102. In the same or other embodiments, the alert personalization application 130 can be integrated into the vehicle 102 in any technically feasible fashion. For instance, in some embodiments, the compute instance 110(2) is included in the instrument cluster 122. In the same or other embodiments, the alert personalization application 130 can reside in the memories 116 of any number of compute instances 110 and execute on the processors 112 of any number of compute instances 110 in any combination.

In some embodiments, the alert personalization application 130 and the DMS application 180 both reside one of the memories 116 and/or both execute on one of the processors 112. In the same or other embodiments, any portion (including all) of the functionality described herein within respect to the alert personalization application 130 and any portion (including all) of the functionality described herein within respect the DMS application 180 are integrated into a single software application.

In some embodiments, the alert personalization application 130 automatically causes the DMS application 180 to modify any number of the alert characteristics 182 to reduce annoyance levels 148 associated with the driver 104 of the vehicle 102 during any number of driving sessions (not shown). As used herein, a "driving session" refers to a period of time during which the vehicle 102 is continuously operating. The annoyance levels 148 are also referred to herein individually as "the annoyance level 148." Each of the annoyance levels 148 is an estimated level of annoyance associated with one or more occupants (e.g., the driver 104) at an associated point in time. Accordingly, over each driving session, the driver 104 is associated with a sequence of annoyance levels 148.

As shown, in some embodiments, the alert personalization application 130 includes, without limitation, an individual profile 160, an annoyance sensing engine 140, and an annoyance reduction engine 170. The individual profile 160 specifies, without limitation, any number and/or types of alert preferences (not shown) directly expressed by the driver 104 of the vehicle 102 in any technically feasible fashion. In some embodiments, the individual profile 160 includes, without limitation, any number and/or types of preferred alert characteristics.

In some embodiments, at the start of each driving session, the alert personalization application 130 acquires the individual profile 160 associated with the driver 104 of the vehicle 102. The alert personalization application 130 can acquire the individual profile 160 in any technically feasible fashion. In some embodiments, the alert personalization application 130 attempts to read the individual profile 160 from any type of memory 116 that can be in any location (e.g., one of the components of the vehicle 102, a cloud environment, etc.) that is accessible to the alert personalization application 130. If the alert personalization application 130 is unable to read the individual profile 160 from the memory 116, then the alert personalization application 130 generates the individual profile 160 that specifies no alert preferences.

During each driving session, the alert personalization application 130 updates the individual profile 160 to reflect any number and/or types of alert preference commands (not shown) issued by the driver 104 via any number and/or type of components of the vehicle 102. In some embodiments, the alert personalization application 130 can receive alert preference commands that are generated in response to input received from the driver 104 via a menu that is included in any type of software application that executes on one of the compute instances 110 included in the vehicle 102. In the same or other embodiments, the alert personalization application 130 can receive alert preference commands that are generated in response to the driver 104 interacting with any number and/or type of interface mechanisms integrated into the vehicle 102. In the same or other embodiments, the alert personalization application 130 can receive alert preference commands that are generated in response to verbal commands issued by the driver 104.

Whenever the alert personalization application 130 acquires and/or updates the individual profile 160, the annoyance reduction engine 170 causes the DMS application 180 to automatically modify the alert characteristics 182 to comply with the individual profile 160. The annoyance reduction engine 170 can cause the DMS application 180 to automatically modify the alert characteristics 182 in any technically feasible fashion.

As shown, in some embodiments, the annoyance reduction engine 170 generates any number of modification specifications 178 during each driving session. The modification specifications 178 are also referred to herein individually as "the modification specification 178." Each of the modification specifications 178 specifies, without limitation any number of modifications to any number of the alert characteristics 182 in any technically feasible fashion. The annoyance reduction engine 170 can generate any number of the modification specifications 178 based on updates to the individual profile 160. As described in greater detail below, the annoyance reduction engine 170 can generate any number of the modification specifications 178 based on negative reactions of the driver 104 to the in-vehicle alerts 188.

Upon generating each of the modification specifications 178, the annoyance reduction engine 170 transmits the modification specification 178 to the DMS application 180. Consequently, over each driving session, the annoyance reduction engine 170 transmits a sequence of the modification specifications 178 to the DMS application 180. Upon receiving each of the modification specifications 178, the DMS application 180 modifies one or more of the alert characteristics 182 as per the modification specification 178.

In some embodiments, after each driving session is complete, the alert personalization application 130 stores the individual profile 160 in any type of memory 116. The memory 116 can be in any location (e.g., one of the components of the vehicle 102, a cloud environment, etc.), that is accessible to the alert personalization application 130. In this fashion, the alert personalization application 130 retains the alert preferences expressed by the driver 104 between driving sessions.

In some embodiments, as the vehicle 102 operates, the alert personalization application 130 continually or repeatedly receives any number and/or types of occupant sensor datasets 152 from the occupant sensors 106. In the same or other embodiments, the vehicle 102, any number of the occupant sensors 106, any number of other components included in the vehicle 102, or any combination thereof can transmit any number and/or types of the occupant sensor datasets 152 to the alert personalization application 130 in any technically feasible fashion. In some embodiments, the alert personalization application 130 can acquire any number and/or types of the occupant sensor datasets 152 from any number of software applications, the vehicle 102, any number of the occupant sensors 106, any number of other components included in the vehicle 102, or any combination thereof in any technically feasible fashion.

In some embodiments, during each driving session, the annoyance sensing engine 140 repeatedly estimates the annoyance level 148 associated with the driver 104 based on the occupant sensor datasets 152 that the annoyance sensing engine 140 has received thus-far. In some embodiments, the annoyance sensing engine 140 estimates the annoyance level 148 associated with the driver 104 continually and/or in real-time. In some other embodiments, the annoyance sensing engine 140 estimates the annoyance level 148 of the driver 104 in response to any number and/or types of trigger (e.g., every second). The annoyance sensing engine 140 can estimate the annoyance level 148 associated with the driver 104 at any point in time in any technically feasible fashion.

As shown, in some embodiments, the annoyance sensing engine 140 includes, without limitation, an auditory annoyance detector 142, a visual annoyance detector 144, and a physiological annoyance detector 146. The auditory annoyance detector 142, the visual annoyance detector 144, and the physiological annoyance detector 146 repeatedly evaluate any amount and/or types of auditory sensor data, visual sensor data, and physiological sensor data, respectively, included in the occupant sensor datasets 152 to provide insight into the annoyance level 148 associated with the driver 104.

In some embodiments, the auditory annoyance detector 142 generates an auditory-based annoyance estimate (not shown) based, at least in part, on simple voice tones and/or words that provide insight into the annoyance level 148 associated with the driver 104. For example, the auditory annoyance detector 142 could generate the auditory-based annoyance estimate based on the tone of voice and/or the words with which the driver 104 responds one of the in-vehicle alerts 188. In the same or other embodiments, the auditory annoyance detector 142 generates an auditory-based annoyance estimate based, at least in part, on any number and/or types of algorithms that perform emotion analysis based on voice.

In some embodiments, the visual annoyance detector 144 generates a visual-based annoyance estimate (not shown) based, at least in part, on facial contortions that are indicative of annoyance, such as eyebrow raising, squinting, etc. In some embodiments, because different cultures and different people use different facial contortions to express annoyance, the visual annoyance detector 144 generates a facial contortion baseline (not shown) for the driver 104 and generates the visual-based annoyance estimate based on computing deviations from the facial contortion baseline. In the same or other embodiments, the visual annoyance detector 144 generates the visual-based annoyance estimate based, at least in part, on techniques that detect and evaluate observable facial landmark action units.

In some embodiments, the visual annoyance detector 144 applies any number and/or type of remote-photoplethysmography techniques to visual sensor data to detect heart rate and/or heart rate variability changes. The visual annoyance detector 144 then computes the visual-based annoyance estimate based, at least in part, on the detected heart rate and/or the heart rate variability changes.

In some embodiments, the physiological annoyance detector 146 generates a physiological-based annoyance estimate (not shown) based, at least in part, on heart rate and/or heart rate variability changes detected via physiological sensor data. In the same or other embodiments, the physiological annoyance detector 146 generates a physiological-based annoyance estimate based at least in part, on galvanic skin response changes and/or changes in a force (e.g., grip force) associated with a steering-wheel using physiological sensor data measured by any number and/or type of steering wheel sensors.

In some embodiments, the annoyance sensing engine 140 repeatedly estimates the annoyance level 148 of the driver 104 at the current point in time based on the auditory-based annoyance estimate, the visual-based annoyance estimate, and the physiological-based annoyance estimate at the current point in time. The annoyance sensing engine 140 can aggregate the auditory-based annoyance estimate, the visual-based annoyance estimate, and the physiological-based annoyance estimate in any technically feasible fashion to compute the annoyance level 148. Furthermore, the auditory annoyance detector 142, the visual annoyance detector 144, the physiological annoyance detector 146, and the annoyance sensing engine 140 can specify the auditory-based annoyance estimate, the visual-based annoyance estimate, the physiological-based annoyance estimate, and the annoyance level 148 with respect to any number and/or types of scales.

Upon computing the annoyance level 148 associated with the current time, the annoyance sensing engine 140 transmits the annoyance level 148 to the annoyance reduction engine 170 in any technically feasible fashion. Accordingly, over the driving session, the annoyance sensing engine 140 transmits a sequence of the annoyance levels 148 to the annoyance reduction engine 170, where each of the annoyance levels 148 is associated with a different point in time. In some embodiments, each of the annoyance levels 148 is associated with a different timestamp that indicates the associated point in time.

As noted previously herein, during the driving session, the annoyance reduction engine 170 can generate any number of the modification specifications 178 based on negative reactions of the driver 104 to one or more of the in-vehicle alerts 188. In some embodiments, the annoyance reduction engine 170 detects negative reactions of the driver 104 to one or more of the in-vehicle alerts 188 based on the annoyance levels 148 and the in-vehicle alerts 188.

To detect negative reactions to in-vehicle alerts 188, the annoyance reduction engine 170 directly and/or indirectly monitors the in-vehicle alerts 188 in any technically feasible fashion. Although not shown, in some embodiments, when the DMS application 180 transmits each of the in-vehicle alerts 188 to the vehicle 102, the DMS application 180 also transmits the in-vehicle alert 188 to the alert personalization application 130.

In some other embodiments, the annoyance reduction engine 170 indirectly monitors the in-vehicle alerts 188 via alert notifications 186. The alert notifications 186 are also referred to herein individually as "the alert notification 186." Each of the alert notifications 186 corresponds to a different one of the in-vehicle alerts 188. When the DMS application 180 generates each of the in-vehicle alerts 188, the DMS application 180 also generates the corresponding alert notification 186. When the DMS application 180 transmits each of the in-vehicle alerts 188 to the vehicle 102, the DMS application 180 also transmits the corresponding alert notification 186 to the annoyance reduction engine 170.

Each of the alert notifications 186 includes, without limitation, any amount and/or type of data associated with the corresponding in-vehicle alert 188. Each of the alert notifications 186 is associated with the same point in time as the corresponding in-vehicle alert 188. In some embodiments, each of the alert notifications 186 is associated with a different timestamp that indicates the point in time associated with the corresponding in-vehicle alert 188. In some embodiments, the annoyance reduction engine 170 receives, over time, a sequence of the alert notifications 186 from the DMS application 180.

The annoyance reduction engine 170 can detect negative reactions of the driver 104 to one or more of the in-vehicle alerts 188 in any technically feasible fashion. As described in greater detail in conjunction with FIG. 2, in some embodiments, the annoyance reduction engine 170 repeatedly computes an annoyance increase (not shown in FIG. 1) associated with the current point in time based on the annoyance levels 148 associated with the driver 104. Upon detecting an annoyance increase that meets an increase criterion (not shown in FIG. 1), the annoyance reduction engine 170 performs any number and type of temporal correlation operations between the annoyance increase and the alert notifications 186 to estimate whether the annoyance increase is associated with a negative reaction to at least one of the in-vehicle alerts 188. Estimating that the annoyance increase is associated with a negative reaction to at least one of the in-vehicle alerts 188 is also referred to herein as detecting a negative reaction to at least one of the in-vehicle alert 188

If, at any point in time, the annoyance reduction engine 170 detects a negative reaction to at least one of the in-vehicle alerts 188, then the annoyance reduction engine 170 generates a new modification specification 178 that is intended to reduce subsequent negative reactions to the in-vehicle alerts 188. The modification specification 178 can specify any number and/or type of modifications to any number of the alert characteristics 182 in any technically feasible fashion. A modification to any number of the alert characteristics 182 is also referred to herein as an "alert modification." In some embodiments, each alert modifications is, without limitation, a replacement characteristic for one of the alert characteristics 182, an addition to the alert characteristics 182, or a deletion from the alert characteristics 182. In the same or other embodiments, the modification specification 178 specifies, without limitation, any number of replacement characteristics for any number of the alert characteristics 182, any number of additions to the alert characteristics 182, any number of deletions from the alert characteristics 182, or any combination thereof.

The annoyance reduction engine 170 can determine the modification specification 178 in any technically feasible fashion. In some embodiments, the annoyance reduction engine 170 implements any number and/or types of rules, any number and/or types of algorithms, any number and/or types of heuristics, any number and/or types of machine learning techniques, any number and/or type of operations, or any combination thereof to determine the modification specification 178 based on any amount and/or types of relevant data.

Figure 2:
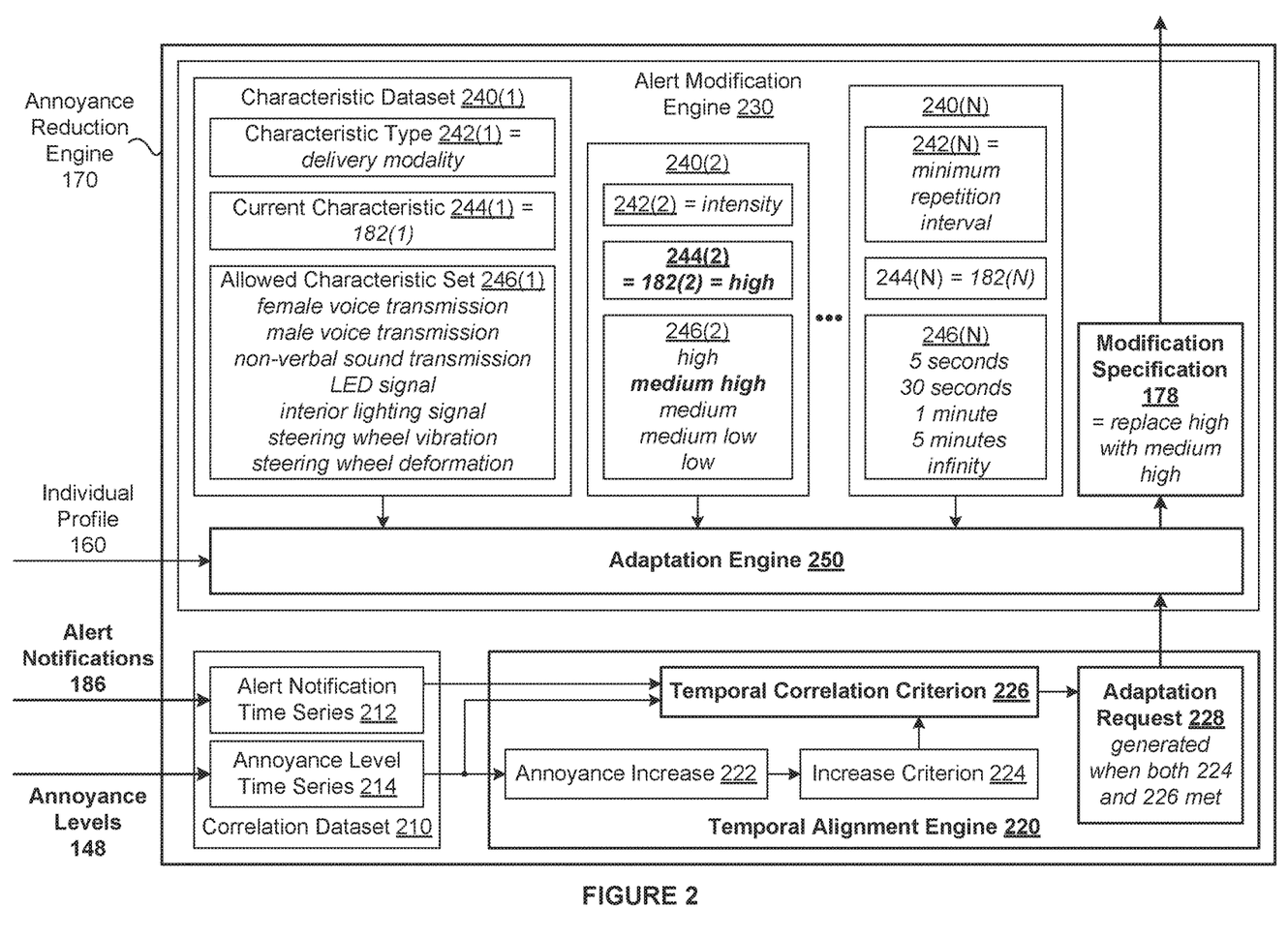
FIG. 2 is a more detailed illustration of the annoyance reduction engine of FIG. 1, according to various embodiments.

In some embodiments, and as described in greater detail in conjunction with FIG. 2, the alert characteristics 182 include, without limitation, a different alert characteristic 182 for each of any number of characteristic types (not shown in FIG. 1). Some examples of characteristic types include, without limitation, delivery modality, intensity, and minimum repetition interval. Each of the characteristic types is associated with a current characteristics (not shown in FIG. 1) that is equal to the corresponding alert characteristic 182 and a different allowed characteristic set (not shown in FIG. 1). The annoyance reduction engine 170 performs any number and/or types of operations to determine any number of replacement characteristics for any number of the alert characteristics 182. In some embodiments, the annoyance reduction engine 170 selects the replacement characteristics based on the allowed characteristic sets while ensuring that the replacement characteristics comply with the individual profile 160. The annoyance reduction engine 170 then generates the modification specification 178 specifying that each of the replacement characteristics should replace the associated alert characteristic 182.

For instance, in some embodiments, the annoyance reduction engine 170 determines and selects one or more of the alert characteristics 182 that should be replaced based on any number and/or types of heuristics, rules, and/or algorithms. The annoyance reduction engine 170 also determines that each of the selected alert characteristics 182 should be replaced with one of the allowed characteristics of the same characteristic type as the selected alert characteristics 182. For each of the selected alert characteristics 182, the annoyance reduction engine 170 selects a replacement characteristic that is not equal to the selected alert characteristic 182 from the allowed characteristic set associated with the selected alert characteristic 182 based on any number and/or types of heuristics, rules, and/or algorithms. For each of the selected alert characteristics 182, if the replacement characteristic does not comply with the individual profile 160, then the annoyance reduction engine 170 selects a different replacement characteristic based on any number and/or types of heuristics, rules, and/or algorithms. The annoyance reduction engine 170 then generates the modification specification 178 specifying, without limitation, that each of the selected alert characteristics 182 should be replaced with the associated replacement characteristic.

For instance, in some embodiments, the annoyance reduction engine 170 randomly determines that the alert characteristic 182 of "male voice transmission" should be replaced. The alert characteristic 182 of "male voice transmission" is a delivery modality. The annoyance reduction engine 170 then randomly selects the replacement characteristic of "steering wheel vibration" from the allowed characteristic set for the characteristic type of delivery modality. The annoyance reduction engine 170 then generates the modification specification 178 specifying that the alert characteristic 182 of "male voice transmission" should be replaced with "steering wheel vibration."

Although not shown, in some embodiments, the annoyance reduction engine 170 generates any number of the modification specifications 178 based, at least in part, on a driving session database and/or a personalized driving database that is generated by the alert personalization application 130. In some embodiments, the driving session database includes, without limitation, any amount and/or types of data that is associated with the current driving session and is relevant to reducing negative reactions to the in-vehicle alerts 188. In the same or other embodiments, the personalized driving database includes, without limitation, any amount and/or types of data that is associated with any number of previous driving sessions that are associated with the driver 104 and is relevant to reducing negative reactions to the in-vehicle alerts 188.

In some embodiments, during each of the driving sessions, the alert personalization application 130 stores the alert characteristics 182, the occupant sensor datasets 152, the alert notifications 186, the annoyance levels 148, and the modification specifications 178 in the driving session database. After the driving session, the alert personalization application 130 adds any amount of the data stored in the driving session database to the personalized training database associated with the driver 104.

Although not shown, in some other embodiments, the alert personalization application 130 uses a trained machine learning model to determine the modification specifications 178. The trained machine learning model can include, without limitation, any number and/or types of machine learning models that are trained in any technically feasible fashion to map different negative reactions to in-vehicle alerts 188 to one or more alert modifications. After mapping a negative reaction to one or more alert modifications via the trained machine learning model, the alert personalization application 130 generates the modification specification 178 that specifies, without limitation, the one or more alert modifications.

In some embodiments, each of any number of drivers 104 are associated with a different trained machine learning model. For each of the drivers 104, any number and type of training operations are performed on an untrained or partially machine learning model based on a personalized training database. Each of the personalized training databases includes, without limitation, any amount and/or types of data that is relevant to reducing any negative reactions of the associated driver 104 to the in-vehicle alerts 188. In some embodiments, each of the personalized training databases includes, without limitation, any number of the alert characteristics 182, the occupant sensor datasets 152, the alert notifications 186, the annoyance levels 148, and the modification specifications 178 for any number of driver sessions.

In some embodiments, at the start of each driving session, the alert personalization application 130 acquires the most recent version of a trained machine learning model associated with the driver 104 or a default trained machine learning model. As described previously herein, during the driving session, the alert personalization application 130 stores the alert characteristics 182, the occupant sensor datasets 152, the alert notifications 186, the annoyance levels 148, and the modification specifications 178 in a driving session database. After the driving session, the alert personalization application 130 adds any amount of the data stored in the driving session database to the personalized training database associated with the driver 104. Subsequently, a training application (not shown) re-trains the trained machine learning model associated with the driver 104 or the default trained machine learning model based on the personalized training database to generate a new version of the trained machine learning model associated with the drier 104.

In this fashion, over time, each of the trained machine learning models learns to tailor the alert characteristics 182 to reduce negative reactions of the associated driver 104 to the in-vehicle alerts 188. In particular, each of the trained machine learning models can learn strategies that mitigate individual patterns of the in-vehicle alerts 188 that lead to negative reactions of the associated drivers 104. In some embodiments, the trained machine learning model could disable one or more types of the in-vehicle alerts 188. For example, the trained machine learning model associated with a given driver 104 could learn to generate alert modifications that disable the in-vehicle alerts 188 associated with watching the road during the first few minutes of each driving session (e.g., when the driver 104 typically backs the vehicle 102 out of a garage).

The annoyance reduction engine 170 can cause the DMS application 180 to implement the modification specifications 178 in any technically feasible fashion. In some embodiments, upon generating the modification specification 178, the annoyance reduction engine 170 transmits the modification specifications 178 to the DMS application 180. Upon receiving each of the modification specifications 178, the DMS application 180 modifies one or more of the alert characteristics 182 as per the modification specification 178.

Note that the techniques described herein are illustrative rather than restrictive and may be altered without departing from the broader spirit and scope of the embodiments. Many modifications and variations will be apparent to those of ordinary skill in the art without departing from the scope and spirit of the described embodiments and techniques. Further, in various embodiments, any number of the techniques disclosed herein may be implemented while other techniques may be omitted in any technically feasible fashion.

In some embodiments, the alert personalization application 130 detects and reduces any number of types of negative reactions to in-vehicle alerts in any technically feasible fashion and the techniques described herein are modified accordingly. For instance, although not shown, in some embodiments, the alert personalization application 130 includes, without limitation, any number of individual profiles 160, a negative emotion sensing engine instead of the annoyance sensing engine 140, and a negative emotion reduction engine instead of the annoyance reduction engine 170.

Each of the individual profiles 160 is associated with a different occupant of the vehicle 102. The alert personalization application 130 acquires, updates, and stores the individual profiles 160 in any technically feasible fashion. The negative emotion reduction engine determines any number of modification specifications 178 based on the individual profiles 160 and/or changes to the individual profiles 160 in any technically feasible fashion. In some embodiments, upon generating the modification specification 178, the negative emotion reduction engine transmits the modification specifications 178 to the DMS application 180.

In some embodiments, the negative emotion sensing engine repeatedly estimates levels of any number of negative emotions or "negative emotion levels" associated with any number of the occupants of the vehicle 102 based on the occupant sensor datasets 152. Some examples of negative emotions include, without limitation, sadness, anger, frustration, annoyance, rage, disgust, guilt, fear, anxiety, etc. The negative emotion sensing engine transmits the negative emotion levels to the negative emotion reduction engine.

The negative emotion reduction engine performs any number and types of operations including, without limitation, any number and/or types of temporal correlation operations based on the negative emotion levels and the alert notifications 186 to estimate negative reactions of any number of the occupants of the vehicle 102 to the in-vehicle alerts 188. In some embodiments, for each estimated negative reaction, the negative emotion reduction engine generates a new modification specification 178 specifying any number of modifications to any number of the alert characteristics 182. Upon generating each of the modification specifications 178, the negative emotion reduction engine transmits the modification specifications 178 to the DMS application 180.

In some embodiments, the alert personalization application 130 detects negative reactions to any number and/or types of the in-vehicle alerts 188 that are generated by any number and/or type of software applications and/or components of the vehicle 102 in any technically feasible fashion. In some embodiments, the alert personalization application 130 detects negative reactions to in-vehicle alerts 188 generated by the vehicle 102 itself warning that one or more of the occupants is not wearing a seat belt while the vehicle 102 is moving. In the same or other embodiments, the alert personalization application 130 modifies any number and/or types of alert characteristics 182 associated with any number of software application and/or components of the vehicle 102 in any technically feasible fashion in response to any types of negative reactions.

In some embodiments, the alert personalization application 130 modifies any number of alert characteristics 182 based on any amount and/or type of data instead of or in addition to any number of the occupant sensor datasets 152, the in-vehicle alerts 188, and the individual profile 160. For instance, in some embodiments, the alert personalization application 130 can modify the alert characteristics 182 based, at least in part, on sensor data received from the outward-facing sensors 126 and/or the vehicle sensors 128. For instance, in some embodiments, the alert personalization application 130 modifies the alert characteristics 182 to reduce the intensity and/or increase the minimum repetition interval of the in-vehicle alerts 188 when the transmission of the vehicle 102 is put into reverse. Subsequently, when the transmission of the vehicle 102 is put into drive, the alert personalization application 130 modifies the alert characteristics 182 to increase the intensity and/or decrease the minimum repetition interval of the in-vehicle alerts 188.

It will be appreciated that the system shown herein is illustrative and that variations and modifications are possible. The connection topology, including the location and arrangement of the vehicle 102, the compute instances 110, the DMS application 180, and the alert personalization application 130 can be modified as desired. In certain embodiments, one or more components shown in FIG. 1 may not be present. For instance, in some alternate embodiments, any amount of the functionality of the alert personalizing application 130 and the DMS application 180 can be subsumed into a single software application.

Reducing Driver Annoyance Associated with
In-Vehicle Alerts

FIG. 2 is a more detailed illustration of the annoyance reduction engine 170 of FIG. 1, according to various embodiments. For explanatory purposes only, FIG. 2 depicts the annoyance reduction engine 170 in the context of generating the modification specification 178 at a current point in time during a driving session and transmitting the modification specification 178 to the DMS application 180 (not shown in FIG. 2). In some embodiments, the annoyance reduction engine 170 generates the modification specification 178 based on the alert notifications 186, the annoyance levels 148, and the individual profile 160.

The annoyance reduction engine 170 includes, without limitation, a correlation dataset 210, a temporal alignment engine 220, and an alert modification engine 230. The correlation dataset 210 includes, without limitation, an alert notification time series 212 and an annoyance level time series 214. At the start of each driving session, the annoyance reduction engine 170 generates the correlation dataset 210 that includes, without limitation, the alert notification time series 212 that has no entries, and the annoyance level time series 214 that has no entries.

As the annoyance reduction engine 170 receives each of the alert notifications 186 from the DMS application 180, the annoyance reduction engine 170 appends the alert notification 186 and an associated timestamp (not shown) to the alert notification time series 212. As the annoyance reduction engine 170 receives each of the annoyance levels 148 from the annoyance sensing engine 140 (not shown in FIG. 2), the annoyance reduction engine 170 appends the annoyance level 148 and an associated timestamp (not shown) to the annoyance level time series 214.

As shown, in some embodiments, the temporal alignment engine 220 includes, without limitation, an annoyance increase 222, an increase criterion 224, a temporal correlation criterion 226, and an adaptation request 228. When the annoyance reduction engine 170 appends a new annoyance level 148 to the annoyance level time series 214, the temporal alignment engine 220 computes the annoyance increase 222. For explanatory purposes only, at any given point in time, the annoyance level 148 that is the last entry included in the annoyance level time series 214 is also referred to herein as the "current annoyance level 148." The annoyance increase 222 quantifies a difference between the current annoyance level 148 and one of the other annoyance levels 148 included in the annoyance level time series 214. In some embodiments, the annoyance increase 222 is associated with the same timestamp as the current annoyance level 148. The temporal alignment engine 220 can compute the annoyance increase 222 in any technically feasible fashion.

In some embodiments, the temporal alignment engine 220 subtracts the annoyance level 148 that immediately precedes the current annoyance level 148 in the annoyance level time series 214 from the current annoyance level 148 to compute the annoyance increase 222. Accordingly, the annoyance increase 222 can be negative, thereby indicating an annoyance decrease. In some other embodiments, the temporal alignment engine 220 divides the current annoyance level 148 by the annoyance level 148 that immediately precedes the current annoyance level 148 in the annoyance level time series 214 to compute the annoyance increase 222 as a ratio.

Although not shown, in yet other embodiments, the temporal alignment engine 220 selects the annoyance levels 148 from the annoyance level time series 214 that are associated with timestamps that are within a comparison time window (e.g., 2 seconds) of the timestamp associated with the current annoyance level 148. For each of the selected annoyance levels 148, the temporal alignment engine 220 subtracts the selected annoyance level 148 from the current annoyance level 148 to compute an annoyance difference. The temporal alignment engine 220 then sets the annoyance increase 222 equal to the maximum of the annoyance differences. In this fashion, the temporal alignment engine 220 captures changes in the annoyance of the driver 104 that occur gradually within the comparison time window.

Subsequently, the temporal alignment engine 220 determines whether or not the annoyance increase 222 meets the increase criterion 224. The increase criterion 224 can specify any number and/or type of conditions that are indicative of a negative reaction. For instance, in some embodiments, the annoyance increase 222 is a ratio and the increase criterion 224 specifies that the annoyance increase 222 is at least 1.2.

If the annoyance increase 222 does not meet the increase criterion 224, then the annoyance reduction engine 170 does not generate the modification specification 178 based on the current annoyance level 148. If, however, the annoyance increase 222 meets the increase criterion 224, then the temporal alignment engine 220 determines whether the annoyance increase 222 is indicative of a negative reaction to one of the in-vehicle alerts 188 based on the annoyance level time series 214, the alert notification time series 212, and the temporal correlation criterion 226.

The temporal correlation criterion 226 specifies any number and/or type of conditions defining any number and/or types of temporal correlations that indicate that the annoyance increase 222 is a negative reaction to at least one of the in-vehicle alerts 188. The temporal alignment engine 220 can perform any number and/or types of temporal correlation operations between the annoyance level time series 214 and the alert notification time series 212 to determine whether or not the annoyance increase 222 meets the temporal correlation criterion 226.

In some embodiments, the temporal correlation criterion 226 specifies that at least one of the in-vehicle alerts 188 occurs within a reaction time interval (not shown) relative to the timestamp associated with the annoyance increase 222 (e.g., a five second interval that ends at the timestamp associated with the annoyance increase 222). The temporal alignment engine 220 determines the reaction time interval based on the timestamp associated with the annoyance increase 222. The temporal alignment engine 220 then selects any of the alert notifications 186 from the alert notification time series 212 that lie within the reaction time interval.

If the temporal alignment engine 220 selects none of the alert notifications 186, then the annoyance increase 222 does not meet temporal correlation criterion 226, and the annoyance reduction engine 170 does not generate the modification specification 178 based on the current annoyance level 148. If, however, the annoyance increase 222 meets both the increase criterion 224 and the temporal correlation criterion 226, then the temporal alignment engine 220 generates the adaption request 228. The adaptation request 228 can specify, without limitation, any amount and/or types of data that is relevant to generating the modification specification 178 in any technically feasible fashion.

In some embodiments, the adaptation request 228 is a trigger that causes the alert modification engine 230 to generate the modification specification 178. In the same or other embodiments, the adaptation request 228 specifies, without limitation, any amount and/or types of data associated with the selected alert notifications 186, the associated in-vehicle alerts 188, the vehicle 102, the driver 104, or any combination thereof. For instance, in some embodiments, the adaptation request 228 specifies, without limitation, a type of the in-vehicle alert 188 (e.g., not looking at the road ahead) and a speed of the vehicle 102. The temporal alignment engine 220 can generate the adaptation request 228 in any technically feasible fashion based on any amount and/or types of data. For instance, in some embodiments, the temporal alignment engine 220 monitors vehicle sensor data generated by the vehicle sensors 128 and generates the adaptation request 228 based, at least in part, on the vehicle sensor data.

If the temporal alignment engine 220 does not generate the adaption request 228, then the annoyance reduction engine 170 does not generates the modification specification 178 based on the current annoyance level 148. Otherwise, the alert modification engine 230 generates the modification specification 178 based on the adaption request 228 and the individual profile 160. The alert modification engine 230 can implement any number and/or types of rules, any number and/or types of algorithms, any number and/or types of heuristics, any number and/or types of machine learning techniques, any number and/or type of operations, or any combination thereof to determine the modification specification 178 based on the adaptation request 228 and the individual profile 160.

As shown, in some embodiments, the alert modification engine 230 includes, without limitation, characteristics datasets 240(1)-240(N), an adaptation engine 250, and the modification specification 178, where N can be any positive integer. The characteristics datasets 240(1)-240(N) are also referred to herein individually as "the characteristics dataset 240" and collectively as "the characteristics datasets 240." The characteristic dataset 240(x), where x in an integer between 1 and N, includes, without limitation, a characteristic type 242(x), a current characteristic 244(x), and an allowed characteristic set 246(x). The characteristic types 242(1)-242(N) are also referred to herein individually as "the characteristic type 242" and collectively as "the characteristic types 242." The current characteristics 244(1)-244(N) are also referred to herein individually as "the current characteristic 244" and collectively as "the current characteristics 244." The allowed characteristic sets 246(1)-246(N) are also referred to herein individually as "the characteristic set 246" and collectively as "the characteristic sets 246."

For the characteristic dataset 240(x), the characteristic type 242(x) specifies a type of an associated alert characteristic 182 included in the DMS application 180, the current characteristic 244(x) specifies the associated alert characteristic 182, and the allowed characteristic set 246(x) specifies any number of allowed characteristics for the characteristic type 242(x). The alert modification engine 230 can determine the characteristics datasets 240 and track the current characteristics 244 in any technically feasible fashion.

Whenever the temporal alignment engine 220 generates a new adaptation request 228, the adaptation engine 250 generates a new modification specification 178 based the new adaptation request 228, the characteristics datasets 240, and the individual profile 160. In the embodiment depicted in FIG. 2, the adaptation engine 250 selects one or more of the current characteristics 244 for replacement based on any number of rules and/or heuristics, any amount and/or types of the data specified via the adaptation request 228, and the individual profile 160. In particular, the adaptation engine 250 does not select for modification any of the current characteristics 244 that are specified via the individual profile 160. In this fashion, the adaptation engine 250 ensures that the modification specification 178 complies with the individual profile 160.

For each of the selected current characteristics 244, the adaptation engine 250 determines a replacement characteristic (not shown) from the allowed characteristic set 246 associated with the current characteristic 244. The adaptation engine 250 can determine the replacement characteristics based on any number of rules and/or heuristics and any amount and/or types of data specified via the adaptation request 228. In some embodiments, the adaptation engine 250 selects the replacement characteristics in a holistic fashion—taking into account all of the selected current characteristics 244 and the associated allowed characteristic sets 246 when determining each of the replacement characteristics.

As described previously herein in conjunction with FIG. 1, in some embodiments the alert personalization application 130 maintains a driving session database (not shown) and/or a personalized driving database (not shown). In some embodiments, the adaptation engine 250 selects any number of the current characteristics 244 for replacement and/or any number of the replacement characteristics based, at least in part, on the driving session database and/or the personalized driving database.

Subsequently, the adaptation engine 250 generates a new modification specification 178 that specifies, without limitation, that each of the selected current characteristics 244 is to be replaced with the associated replacement characteristic. The adaptation engine 250 transmits the modification specification 178 to the DMS application 180. For each of the selected current characteristics 244, the adaptation engine 250 sets the current characteristic 244 equal to the associated replacement characteristic, thereby mirroring the changes to the alert characteristics 182 specified via the modification specification 178.

For explanatory purposes only, exemplary values for some of the characteristic types 242, some of the current characteristics 244, some of the allowed characteristic sets 246, and the modification specification 178 are specified in italics. As shown, the characteristic type 242(1) is delivery modality, the current characteristic 244(1) is equal to the alert characteristic 182(1), and the allowed characteristic set 246(1) includes, without limitation, a female voice transmission, a male voice transmission, a non-verbal sound transmission, a light-emitting diode ("LED") signal, an interior lighting signal, a steering wheel vibration, and a steering wheel deformation. The characteristic type 242(2) is intensity, the current characteristic 244(2) is equal to the alert characteristic 182(2) of high, and the allowed characteristic set 246(2) includes, without limitation, high, medium high, medium, medium low, and low. The characteristic type 242(N) is a minimum repetition interval, where the in-vehicle alert 188 is not to be repeated until the interval of time specified by the minimum repetition interval elapses. The current characteristic 244(N) is equal to the alert characteristic 182(N), and the allowed characteristic set 246(N) includes, without limitation, five seconds, thirty seconds, one minute, five minutes, and infinity (i.e., no in-vehicle alerts 188 are to be generated).

The adaptation engine 250 selects the current characteristic 244(2) of high for replacement. As shown, the current characteristic 244(2) is associated with the characteristic type 242(2) of intensity. To reduce the annoyance associated with the driver 104, the adaptation engine 250 selects the reduced intensity of medium high from the allowed characteristic set 246(2) associated with the characteristic type 242(2) of intensity. The adaptation engine 250 generates a new modification specification 178 that specifies, without limitation, that high is to be replaced with medium high. The adaptation engine 250 transmits the modification specification 178 to the DMS application 180. In response, the DMS application 180 replaces the alert characteristics 182(2) of high with a new alert characteristic 182(N+1), not shown, of medium high.

Figure 3:
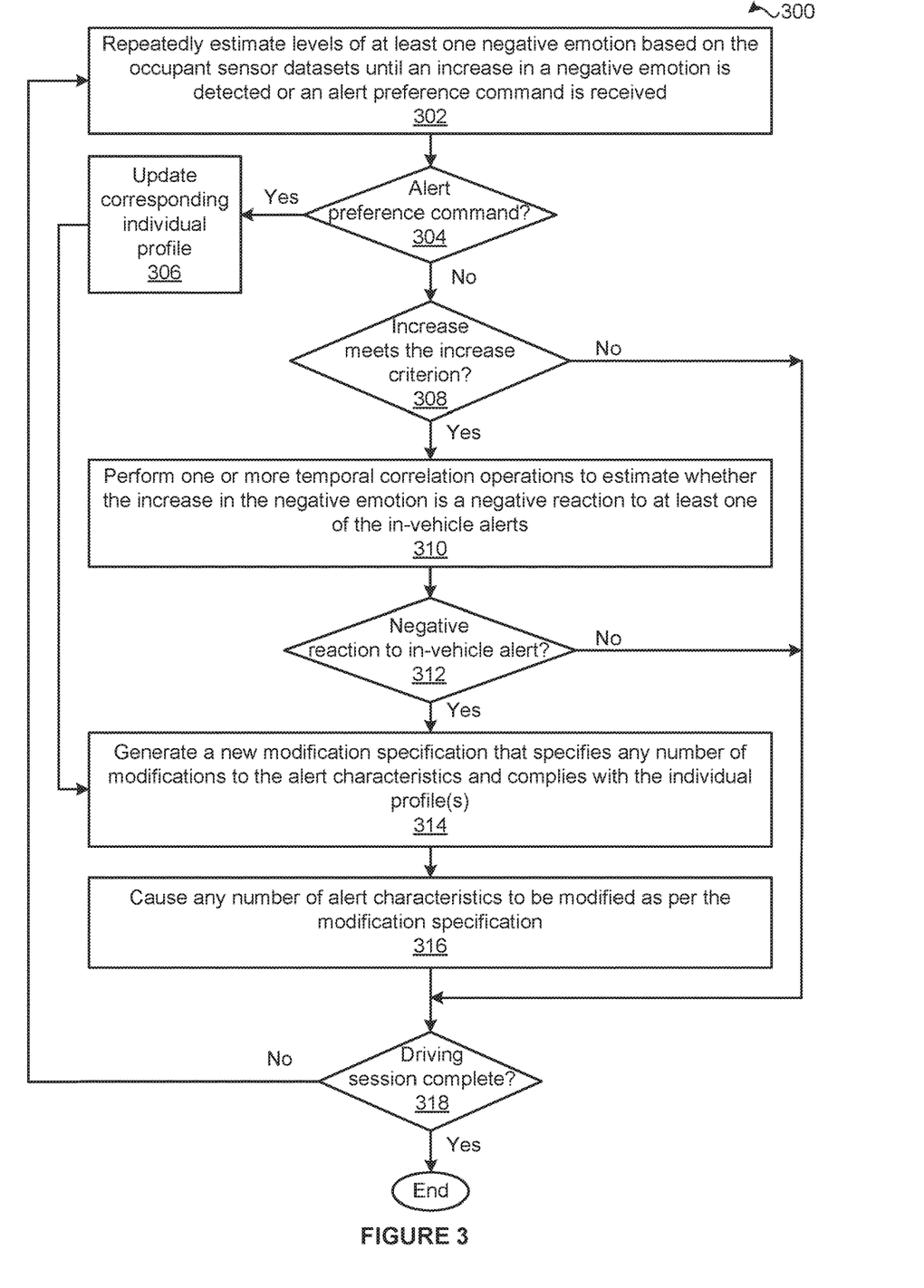
FIG. 3 is a flow diagram of method steps for generating personalized in-vehicle alerts, according to various embodiments.

FIG. 3 is a flow diagram of method steps for generating personalized in-vehicle alerts, according to various embodiments. Although the method steps are described with reference to the systems of FIGS. 1-2, persons skilled in the art will understand that any system configured to implement the method steps, in any order, falls within the scope of the embodiments.

As shown, a method 300 begins at step 302, where the alert personalization application 130 repeatedly estimates levels of at least one negative emotion based on the occupant sensor datasets 152 until an increase in a negative emotion is detected or an alert preference command is received. At step 304, the alert personalization application 130 determines whether the alert personalization application 130 has received an alert preference command.

If, at step 304, the alert personalization application 130 determines that the alert personalization application 130 has received an alert preference command, then the method 300 proceeds to step 306. At step 306, the alert personalization application 130 updates the individual profile 160 associated with the alert preference command to reflect the alert preference(s) specified in the alert preference command. The method 300 then proceeds directly to step 314.

If, however, at step 304, the alert personalization application 130 determines that the alert personalization application 130 has not received an alert preference command, then the method 300 proceeds directly to step 308. At step 308, the alert personalization application 130 determines whether the increase in the negative emotion meets the increase criterion 224 associated with the negative emotion. If, at step 308, the alert personalization application 130 determines that the increase in the negative emotion does not meet the increase criterion 224 associated with the negative emotion, then the method 300 proceeds directly to step 318.

If, however, at step 308, the alert personalization application 130 determines that the increase in the negative emotion meets the increase criterion 224 associated with the negative emotion, then the method 300 proceeds to step 310. At step 310, the alert personalization application 130 performs one or more temporal correlation operations to estimate whether the increase in the negative emotion is a negative reaction to at least one of the in-vehicle alerts 188.

At step 312, the alert personalization application 130 determines whether the alert personalization application 130 has estimated that the negative emotion is a negative reaction to at least one of the in-vehicle alerts 188. If, at step 312, the alert personalization application 130 determines that the alert personalization application 130 has estimated that the negative emotion is not a negative reaction to at least one of the in-vehicle alerts 188, then the method 300 proceeds directly to step 318.

If, however, at step 312, the alert personalization application 130 determines that the alert personalization application 130 has estimated that the negative emotion is a negative reaction to at least one of the in-vehicle alerts 188, then the method 300 proceeds to step 314.

At step 314, the alert personalization application 130 generates a new modification specification 178 that specifies, without limitation, any number of modifications to the alert characteristics 182 and complies with the individual profile(s) 160. At step 316, the alert personalization application 130 causes any number of the alert characteristics 182 to be modified as per the modification specification 178.

At step 318, the alert personalization application 130 determines whether the driving session is complete. If, at step 318, the alert personalization application 130 determines that the driving session is complete, then the method 300 terminates.

If, however, at step 318, the alert personalization application 130 determines that the driving session is not complete, then the method 300 returns to step 302, where the alert personalization application 130 repeatedly estimates levels of at least one negative emotion based on the occupant sensor datasets 152. The method 300 continues to cycle through steps 302-318 until the alert personalization application 130 determines that the driving session is complete at step 318.

In sum, the disclosed techniques can be used to increase the effectiveness of in-vehicle alerts for individual drivers. In one embodiment, an alert personalization application dynamically modifies alert characteristics that influence, without limitation, the delivery modality, the intensity, and the minimum repetition interval associated with in-vehicle alerts generated by a DMS application The vehicle includes, without limitation, any number and/or types of occupant sensors that detect and relay physiological data associated with any number of occupants of the vehicle to the alert personalization application and the DMS application. The DMS application can generate any number of in-vehicle alerts at any points in time based on the physiological data and the alert characteristics. Upon generating a new in-vehicle alert, the driver monitoring system application transmits the in-vehicle alert to the vehicle and transmits a new alert notification to the alert personalization application. In response to the new alert notification, an annoyance reduction engine included in the alert personalization application adds the alert notification to an alert notification time series.

The alert personalization application includes, without limitation, an individual profile, an annoyance sensing engine, and the annoyance reduction engine. The individual profile specifies any alert preferences directly expressed by a driver of the vehicle. At any given time, the alert personalization application can change the individual profile based on any number of alert preference commands received from the driver. If the individual profile changes, then the annoyance reduction engine generates a modification specification that specifies any number of replacements for any number of alert characteristics as per the individual profile. The annoyance reduction engine then transmits the modification specification to the DMS application and, in response, the DMS application replaces at least one of the alert characteristics.

The annoyance sensing engine repeatedly estimates an annoyance level associated with the driver. When the annoyance engine estimates a new annoyance level, the annoyance sensing engine transmits the annoyance level to the annoyance reduction engine. In response, the annoyance reduction engine adds the alert notification to an alert notification time series and computes an associated annoyance increase. The annoyance reduction engine determines whether the annoyance increase meets an increase criterion (e.g., a minimum of a 20% increase). If the annoyance increase meets the increase criterion, then the annoyance reduction engine performs any number and/or types of temporal correlation operations between the annoyance increase and the alert notification time series to estimate whether the annoyance increase is associated with a negative reaction to one or more of the in-vehicle alerts.

If the annoyance reduction engine estimates that the annoyance increase is associated with a negative reaction to an in-vehicle alert, then the annoyance reduction engine generates a modification specification that specifies, without limitation, any number of replacement characteristics for any number of alert characteristics. Notably, the modification specification complies with the individual profile and is intended to reduce annoyance associated with subsequent in-vehicle alerts. The annoyance reduction engine then transmits the modification specification to the DMS application and, in response, the DMS application replaces at least one of the alert characteristics as per the modification specification.

At least one technical advantage of the disclosed techniques relative to the prior art is that the alert personalization application personalizes how and/or when the DMS application generates current and subsequent in-vehicle alerts based on negative reactions of individual driver to prior in-vehicle alerts. In particular, monitoring occupant sensor datasets and in-vehicle alert notifications to automatically detect when an in-vehicle alert causes the annoyance level of a driver to increase and, in response, modifying one or more alert characteristics associated with the DMS application can increase the effectiveness of subsequent in-vehicle alerts. As a result, modifying the alert characteristics can reduce the likelihood that the driver becomes discouraged from using the DMS or paying attention to in-vehicle alerts. In this fashion, the alert personalization application can improve driver safety across a wider variety of drivers relative to prior art approaches to generating in-vehicle alerts. These technical advantages provide one or more technological advancements over prior art approaches.

1. In some embodiments, a computer-implemented method for generating personalized in-vehicle alerts comprises estimating an increase in a negative emotion associated with an occupant of a vehicle based on at least one characteristic of the occupant, determining that the increase is associated with a negative reaction to a first in-vehicle alert that has a first alert characteristic, in response, determining that the first alert characteristic should be replaced with a second alert characteristic, and causing at least a second in-vehicle alert to be generated that has the second alert characteristic instead of the first alert characteristic.

2. The computer-implemented method of clause 1, wherein determining that the increase is associated with the negative reaction comprises performing at least one temporal correlation operation based on a first point in time associated with the increase and a second point in time associated with the first in-vehicle alert.

3. The computer-implemented method of clauses 1 or 2, wherein estimating the increase comprises computing at least one deviation from a facial contortion baseline associated with the occupant based on the at least one characteristic of the occupant.

4. The computer-implemented method of any of clauses 1-3, wherein determining that the first alert characteristic should be replaced with the second alert characteristic comprises determining that the first alert characteristic comprises a first characteristic type, determining that the first alert characteristic should be replaced with a different alert characteristic that also comprises the first characteristic type, and selecting the second alert characteristic from a plurality of alert characteristics that comprise the first characteristic type.

5. The computer-implemented method of any of clauses 1-4, wherein determining that the first alert characteristic should be replaced with the second alert characteristic comprises determining a first alert modification based on the negative reaction and a trained machine learning model that maps different negative reactions to one or more alert modifications, wherein the first alert modification specifies that the first alert characteristic should be replaced with the second alert characteristic.

6. The computer-implemented method of any of clauses 1-5, wherein the negative emotion comprises annoyance, anger, sadness, or frustration.

7. The computer-implemented method of any of clauses 1-6, wherein the first alert characteristic comprises a delivery modality, an intensity, or a minimum repetition interval associated with the first in-vehicle alert.

8. The computer-implemented method of any of clauses 1-7, wherein the at least one characteristic comprises at least one of a facial contortion, a voice tone, a heart rate, a galvanic skin response, or a force associated with a steering-wheel.

9. The computer-implemented method of any of clauses 1-8, wherein the first in-vehicle alert characteristic comprises a delivery modality, and the delivery modality comprises a voice transmission, a non-verbal sound transmission, a light-emitting diode signal, an interior lighting signal, a steering wheel vibration, or a steering wheel deformation.

10. The computer-implemented method of any of clauses 1-9, further comprising estimating another increase in the negative emotion associated with the occupant, determining that the another increase in the negative emotion is associated with another negative reaction to the second in-vehicle alert, and in response, disabling a type of in-vehicle alert that the second in-vehicle alert comprises.

11. In some embodiments, one or more non-transitory computer readable media include instructions that, when executed by one or more processors, cause the one or more processors to generate personalized in-vehicle alerts by performing the steps of estimating an increase in a negative emotion associated with an occupant of a vehicle based on at least one characteristic of the occupant, determining that the increase is associated with a negative reaction to a first in-vehicle alert that has a first alert characteristic, in response, determining that the first alert characteristic should be replaced with a second alert characteristic, and causing at least a second in-vehicle alert to be generated that has the second alert characteristic instead of the first alert characteristic.

12. The one or more non-transitory computer readable media of clause 11, wherein determining that the increase is associated with the negative reaction comprises performing at least one temporal correlation operation based on a first point in time associated with the increase and a second point in time associated with the first in-vehicle alert.

13. The one or more non-transitory computer readable media of clauses 11 or 12, wherein estimating the increase comprises evaluating at least one observable facial landmark action unit based on the at least one characteristic of the occupant.

14. The one or more non-transitory computer readable media of any of clauses 11-13, wherein determining that the first alert characteristic should be replaced with the second alert characteristic comprises determining that the first alert characteristic comprises a first characteristic type, determining that the first alert characteristic should be replaced with a different alert characteristic that also comprises the first characteristic type, and selecting the second alert characteristic from a plurality of alert characteristics that comprise the first characteristic type.

15. The one or more non-transitory computer readable media of any of clauses 11-14, wherein determining that the first alert characteristic should be replaced with the second alert characteristic comprises determining a first alert modification based on the negative reaction and a trained machine learning model that maps different negative reactions to one or more alert modifications, wherein the first alert modification specifies that the first alert characteristic should be replaced with the second alert characteristic.

16. The one or more non-transitory computer readable media of any of clauses 11-15, wherein the negative emotion comprises annoyance, anger, sadness, or frustration.

17. The one or more non-transitory computer readable media of any of clauses 11-16, wherein the first alert characteristic comprises a delivery modality, an intensity, or a minimum repetition interval associated with the first in-vehicle alert.

18. The one or more non-transitory computer readable media of any of clauses 11-17, further comprising determining the at least one characteristic based on data received from at least one of an electroencephalogram sensor, a heart rate sensor, a breathing rate sensor, a pulse oximeter, a galvanic skin response sensor, a camera, or a microphone while the vehicle is operating.

19. The one or more non-transitory computer readable media of any of clauses 11-18, wherein the occupant comprises a driver of the vehicle.

20. In some embodiments, a system comprises at least one memory storing instructions, and at least one processor coupled to the at least one memory that, when executing the instructions, perform the steps of estimating an increase in a negative emotion associated with an occupant of a vehicle based on at least one characteristic of the occupant, determining that the increase is associated with a negative reaction to a first in-vehicle alert that has a first alert characteristic, in response, determining that the first alert characteristic should be replaced with a second alert characteristic, and causing at least a second in-vehicle alert to be generated that has the second alert characteristic instead of the first alert characteristic.

Any and all combinations of any of the claim elements recited in any of the claims and/or any elements described in this application, in any fashion, fall within the contemplated scope of the embodiments and protection.

The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module," a "system," or a "computer." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program code embodied thereon.

Any combination of one or more computer readable media may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory, a Flash memory, an optical fiber, a portable compact disc read-only memory (CD-ROM), an optical storage device, a magnetic storage device, or any suitable combination of the foregoing. In the context of this document, a computer readable storage medium can be any tangible medium that can contain or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A computer-implemented method for generating personalized in-vehicle alerts, the method comprising:
  detecting an increase in a negative emotion associated with an occupant of a vehicle based on at least one characteristic of the occupant;

in response to detecting the increase in negative emotion, determining a reaction time interval that ends at a time associated with the increase in the negative emotion;

determining that the increase is associated with a negative reaction to a first in-vehicle alert based on an occurrence of the first in-vehicle alert within the reaction time interval, wherein the first in-vehicle alert has a first alert characteristic;

in response, determining that the first alert characteristic should be replaced with a second alert characteristic; and causing at least a second in-vehicle alert to be generated that has the second alert characteristic instead of the first alert characteristic.

2. The computer-implemented method of claim 1, wherein determining that the increase is associated with the negative reaction comprises performing at least one temporal correlation operation based on a first point in time associated with the increase and a second point in time associated with the first in-vehicle alert.

3. The computer-implemented method of claim 1, wherein estimating the increase comprises computing at least one deviation from a facial contortion baseline associated with the occupant based on the at least one characteristic of the occupant.

4. The computer-implemented method of claim 1, wherein determining that the first alert characteristic should be replaced with the second alert characteristic comprises:
determining that the first alert characteristic comprises a first characteristic type;
determining that the first alert characteristic should be replaced with a different alert characteristic that also comprises the first characteristic type; and
selecting the second alert characteristic from a plurality of alert characteristics that comprise the first characteristic type.

5. The computer-implemented method of claim 1, wherein determining that the first alert characteristic should be replaced with the second alert characteristic comprises determining a first alert modification based on the negative reaction and a trained machine learning model that maps different negative reactions to one or more alert modifications, wherein the first alert modification specifies that the first alert characteristic should be replaced with the second alert characteristic.

6. The computer-implemented method of claim 1, wherein the negative emotion comprises annoyance, anger, sadness, or frustration.

7. The computer-implemented method of claim 1, wherein the first alert characteristic comprises a delivery modality, an intensity, or a minimum repetition interval associated with the first in-vehicle alert.

8. The computer-implemented method of claim 1, wherein the at least one characteristic comprises at least one of a facial contortion, a voice tone, a heart rate, a galvanic skin response, or a force associated with a steering-wheel.

9. The computer-implemented method of claim 1, wherein the first alert characteristic comprises a delivery modality, and the delivery modality comprises a voice transmission, a non-verbal sound transmission, a light-emitting diode signal, an interior lighting signal, a steering wheel vibration, or a steering wheel deformation.

10. The computer-implemented method of claim 1, further comprising:
estimating another increase in the negative emotion associated with the occupant;
determining that the another increase in the negative emotion is associated with another negative reaction to the second in-vehicle alert; and
in response, disabling a type of in-vehicle alert that the second in-vehicle alert comprises.

11. One or more non-transitory computer readable media including instructions that, when executed by one or more processors, cause the one or more processors to generate personalized in-vehicle alerts by performing the steps of:
detecting an increase in a negative emotion associated with an occupant of a vehicle based on at least one characteristic of the occupant;
in response to detecting the increase in negative emotion, determining a reaction time interval that ends at a time associated with the increase in the negative emotion;
determining that the increase is associated with a negative reaction to a first in-vehicle alert based on an occurrence of the first in-vehicle alert within the reaction time interval, wherein the first in-vehicle alert has a first alert characteristic;
in response, determining that the first alert characteristic should be replaced with a second alert characteristic; and
causing at least a second in-vehicle alert to be generated that has the second alert characteristic instead of the first alert characteristic.

12. The one or more non-transitory computer readable media of claim 11, wherein determining that the increase is associated with the negative reaction comprises performing at least one temporal correlation operation based on a first point in time associated with the increase and a second point in time associated with the first in-vehicle alert.

13. The one or more non-transitory computer readable media of claim 11, wherein estimating the increase comprises evaluating at least one observable facial landmark action unit based on the at least one characteristic of the occupant.

14. The one or more non-transitory computer readable media of claim 11, wherein determining that the first alert characteristic should be replaced with the second alert characteristic comprises:
determining that the first alert characteristic comprises a first characteristic type;
determining that the first alert characteristic should be replaced with a different alert characteristic that also comprises the first characteristic type; and
selecting the second alert characteristic from a plurality of alert characteristics that comprise the first characteristic type.

15. The one or more non-transitory computer readable media of claim 11, wherein determining that the first alert characteristic should be replaced with the second alert characteristic comprises determining a first alert modification based on the negative reaction and a trained machine learning model that maps different negative reactions to one or more alert modifications, wherein the first alert modification specifies that the first alert characteristic should be replaced with the second alert characteristic.

16. The one or more non-transitory computer readable media of claim 11, wherein the negative emotion comprises annoyance, anger, sadness, or frustration.

17. The one or more non-transitory computer readable media of claim 11, wherein the first alert characteristic comprises a delivery modality, an intensity, or a minimum repetition interval associated with the first in-vehicle alert.

18. The one or more non-transitory computer readable media of claim 11, further comprising determining the at least one characteristic based on data received from at least one of an electroencephalogram sensor, a heart rate sensor, a breathing rate sensor, a pulse oximeter, a galvanic skin response sensor, a camera, or a microphone while the vehicle is operating.

19. The one or more non-transitory computer readable media of claim 11, wherein the occupant comprises a driver of the vehicle.

20. A system, comprising:
at least one memory storing instructions; and
at least one processor coupled to the at least one memory that, when executing the instructions, perform the steps of:
detecting an increase in a negative emotion associated with an occupant of a vehicle based on at least one characteristic of the occupant;
in response to detecting the increase in negative emotion, determining a reaction time interval that ends at a time associated with the increase in the negative emotion;
determining that the increase is associated with a negative reaction to a first in-vehicle alert based on an occurrence of the first in-vehicle alert within the reaction time interval, wherein the first in-vehicle alert has a first alert characteristic;
in response, determining that the first alert characteristic should be replaced with a second alert characteristic; and
causing at least a second in-vehicle alert to be generated that has the second alert characteristic instead of the first alert characteristic.

\* \* \* \* \*